US006645483B2

(12) United States Patent
McGhee

(10) Patent No.: US 6,645,483 B2
(45) Date of Patent: Nov. 11, 2003

(54) LUBRICIOUS COATING

(75) Inventor: Diane McGhee, Hazelwood, MO (US)

(73) Assignee: Sherwood Services AG (CH)

( * ) Notice: Subject to any disclaimer, the term of this patent is extended or adjusted under 35 U.S.C. 154(b) by 0 days.

(21) Appl. No.: 09/739,577

(22) Filed: Dec. 18, 2000

(65) Prior Publication Data

US 2001/0051669 A1 Dec. 13, 2001

Related U.S. Application Data

(63) Continuation-in-part of application No. 09/168,031, filed on Oct. 7, 1998, now abandoned.

(51) Int. Cl.$^7$ ...................... A61K 31/74; A61K 31/765; A61K 31/785
(52) U.S. Cl. ................. 424/78.08; 424/78.31; 424/78.32; 424/78.35; 424/78.36; 424/78.37; 424/78.38; 523/112; 523/122; 427/405
(58) Field of Search .................. 523/112, 122; 427/2.25, 2.28, 2.3; 424/78.08, 78.31, 78.32, 78.35, 78.36, 78.37, 78.38, 405

(56) References Cited

U.S. PATENT DOCUMENTS

| 3,939,049 A | | 2/1976 | Ratner et al. | |
| 3,975,350 A | | 8/1976 | Hudgin et al. | |
| 3,987,497 A | | 10/1976 | Stoy et al. | |
| 4,100,309 A | | 7/1978 | Micklus et al. | ................. 427/2 |
| 4,119,094 A | | 10/1978 | Micklus et al. | ......... 128/132 R |
| 4,467,073 A | * | 8/1984 | Creasy | ........................ 525/127 |
| 4,769,013 A | * | 9/1988 | Lorenz et al. | .............. 604/265 |
| 5,091,205 A | * | 2/1992 | Fan | ................................ 427/2 |
| 5,295,978 A | | 3/1994 | Fan et al. | .................... 604/265 |

FOREIGN PATENT DOCUMENTS

| WO | WO 99/19004 | 4/1999 | ........... A61L/27/00 |
| WO | WO 00/44414 | 8/2000 | ........... A61L/27/50 |

* cited by examiner

Primary Examiner—Ana Woodward
(74) Attorney, Agent, or Firm—Mark S. Leonardo; John C. Serio; Brown Rudnick Berlack Israels LLP

(57) ABSTRACT

A lubricant coating vehicle for medical devices used to reduce the coefficient of friction of such devices upon exposure thereof to moisture. The lubricant coating vehicle allows the introduction of a pharmacological additive having a release rate that is within acceptable pharmacokinetic criteria. The release rate is adjusted by utilizing different salt forms of the additive and adjusting the concentration of a urethane pre-polymer.

20 Claims, No Drawings

LUBRICIOUS COATING

CROSS-REFERENCE TO RELATED APPLICATIONS

This Patent Application is a Continuation-In-Part of U.S. application Ser. No. 09/168,031 filed Oct. 7, 1998, NOW ABN the contents of which are incorporated herein by reference in its entirety.

BACKGROUND

1. Technical Field

The present invention relates to a lubricant coating for medical devices, and more particularly, to a hydrophilic polymeric coating which aids medical devices to become slippery when wetted. The lubricant coating of the present invention may be employed to reduce the coefficient of friction of catheters, arterial venous shunts, gastroenteric feed tubes, endotracheal tubes and other medical implants or polymeric substrates. The coating of the present invention also incorporates additive compounds such as anti-microbial that are released in a pharmaceutically acceptable manner. Methods are also provided for the manufacture of the subject lubricant coating and for the application of the same to surfaces of medical devices.

2. Background of the Related Art

Known lubricant coatings applied to surfaces of medical devices include coatings of polyvinylpyrrolidone, polyurethane, acrylic polyester, vinyl resin, fluorocarbons, silicone rubber, and combinations of these substances. For example, Micklus et al., U.S. Pat. Nos. 4,100,309 and 4,119,094, relate to a hydrophilic coating of polyvinylpyrrolidone-polyurethane interpolymer formed using polyisocyanate. Ratner et al., U.S. Pat. No. 3,939,049, relates to a method of grafting hydrogels for lubrication to polymeric substrates using radiation. Hungton et al., U.S. Pat. No. 3,975,350, relates to hydrophilic polyurethane polymers for use as lubricants. Storey. et al. U.S. Pat. No. 3,987,497, relates to a tendon prosthesis having a lubricant hydrogel coating. Many known lubricious coatings are prone to various disadvantages when used in the medical field. Disadvantages of such known lubricants may include insufficiently low coefficient of friction, lack of permanence such as characteristic of silicone or fluorocarbon based coatings, slipperiness when dry as well as wet thus making handling difficult, utilization of hazardous solvents in the manufacture of the same and utilization of unstable reactive materials in the manufacture of the same. Lubricants produced for medical use from unstable reactive material often require the coating solution to be prepared daily or more frequently to be useful and thereby increases waste and expense. Lubricants produced for medical use involving hazardous solvents are undesirable due to patient toxicity concerns and OSHA considerations. Also, lubricant coatings provided for inducing foreign devices into various areas of the body that are susceptible to infection and or thrombogenic reactions have failed to provide a pharmaceutically acceptable carrier for anti-microbial and anti-thrombogenic compounds.

In order to solve these and other potential disadvantages of known lubricants such as those of the above-cited patents incorporated herein by reference, a lubricant coating is needed which when wetted has sufficient lubricity to be useful in the medical device field such as for medical implants and the ability to incorporate within that coating anti-microbial compounds that can be released in a pharmaceutically acceptable manner. The lubricant coating must be capable of adhering to a wide variety of substrates and resist wet abrasion. It would also be desirable to have such a lubricant coating prepared from chemically stable and bio-compatible solvents.

SUMMARY OF THE INVENTION

The present invention provides a lubricant coating composition comprising a hydrophilic polymer comprising polyvinylpyrrolidone, polyoxyethylene-based isocyanate-terminated prepolymer, ethyl lactate and toluene. The present invention also provides a method of making the subject lubricant coating which adheres to a wide variety of substrates and resists wet abrasion. The subject lubricant coating is chemically stable and is bio-compatible as described in greater detail below.

A method for using the subject lubricant coating composition to coat medical devices is provided herein which involves cleaning or washing, drying, dip coating or applying of the lubricant, air drying or removal of excess lubricant, optionally baking and packaging a medical device either before or after sterilization thereof.

The present invention also provides a medical device whereby at least a portion thereof is coated with the subject lubricant coating which is characterized as being able to achieve a wetted lubricity with a reduction of friction of more than fifty (50) percent.

The present invention also provides a vehicle for incorporating an anti-microbial or anti-thrombogenic agent having pharmaceutically acceptable pharmacokinetic properties without interfering with the lubricous nature of the coating.

DETAILED DESCRIPTION OF THE INVENTION

The lubricant coating of the present invention has been found particularly useful in lowering the coefficient of friction of medical devices such as indwelling thoracic catheters and other medical devices. The subject coating is manufactured from a blend of one or more C1–12 alkylbenzenes such as, for example, toluene, xylene, or styrene but preferably toluene to increase stability, a C1–12 alkylester of a carboxylic acid such as for example, ethyl lactate, methylbenzoate, or propolyacrylate wherein ethyl lactate is preferred to increase stability, a polymer such as for example polyvinylpyrrolidone, polyvinyl alcohol, polyacrylic acid or polyethylene oxide, but preferably polyvinylpyrrolidone to increase hydrophilicity and lubricity, and an isocyanate-terminated prepolymer such as, for example, polyoxyethylene-based isocyanate such as a toluene or isophorone diisocyanate-based prepolymer such as for example Hypol* PreMA G60 manufactured by Hampshire Corporation, Lexington, Mass., or Vibrathane® a 4,4-diphenylmethane-disocyanante (MDI) an urethane prepolymer manufactured by Uniroyal, or Pellethane an aromatic ether polyurethane manufactured by Dow Chemical, or Hyrothane manufactured by CardioTech international and or Adiprene® a low-free TDI manufactured by Uniroyal Chemical.

The urethane increases the binding strength of the coating and controls the rate of release and thus enables the pharmacokinetics of the anti-microbial or other pharmacological additive to be within acceptable pharmaceutical limits and it covalently binds anti-thrombogenic additives to prevent systematic absorption. While different urethanes have different properties and may require different solvent systems, the durometer of the urethane must match the durometer of the medical device to be coated or the functionality of the medical device may become compromised. Solvent selection and blend ration are important to provide adequate solubility and inertness to the hydrophilic urethane and additives. Anti-microbials additives, such as silver salts or antibiotics, may be uniformly suspended within the coating solution. These additives are released on contact with moisture, the rate of release and the lubricious properties of the coating are controlled by altering the ratio of urethane and PVP For further examples of suitable polyisocyanates see Encyclopedia of Polymer Science and Technology, H. F. Mark, N. G. Gaylord and N. M. Bikeles (eds.) (1969) incorporated herein by reference.

Anti-microbial additives utilized within this present invention include the biguanides, especially chlorhexidine and its salts, including chorhexidene acetate, chlorhexideine gluconate, chlorhexidine hydrochloride, and chlorhexidine sulfate, silver and its salts, including silver acetate, silver benzoate, silvercarbonate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampician, bacitracin, neomycin, chloramphenical, miconazole, tolnaftate,quinolone such as oxolinic acid, norfloxacin, nalidix acid, pefloxacin, enoxacin and ciprofloxacin, penicillins such as ampicillin, amoxicillin and piracil, cephalosporins, vancomycin, and combinations of any of the above anti-microbials.

An anti-thrombromgenic additive useful according to this present invention would be heparin. Additionally, organic compounds derived from plants and herbs having desirable pharmacological properties can be utilized. Extracts of plants and herbs have been know to posses anti-microbial activity and their use has been shown to be safe for human and animal consumption. Extracts of such plants, known as phytochemicals, may be utilized for their anti-microbial properties. Some of these extracts, such as grapefruit seed extract, Tea Tree Oil and Myrtle Oil and others can be incorporated into the lubricious coating vehicle and their anti-microbial properties released to the surrounding tissue in an efficacious manner.

In some illustrative embodiments of the present invention colorants, emulsifiers, surfactants, and color stabilizers that are well known within the art are added to the coating formulation. The colorants in the form of dyes or pigments aid in reducing shelf life discoloration or discoloration due to the effects of sterilization. The addition of emulsifiers and surfactants aid in suspension stability of the lubricous coating vehicle and surface wettability. Color stabilizers are sometimes added when the anti-microbial is a silver salt.

The release rate of the pharmacological additive within the lubricious coating and the lubricity of the coating can be controlled by the adjustment of the concentration of the urethane pre-polymer and the concentration of PVP.

The lubricant coating vehicle of the present invention is generally prepared by first obtaining a mixing vat in which to prepare the solution. The mixing vat should be dry and free of water and alcohol. The present lubricant coating vehicle composition is preferably blended at room temperature according to the following component ratios described as follows in weight percent: 1 to 4 weight percent but preferably 1.9 weight percent polyvinylpyrrolidone, 0.5 to 3 weight percent but preferably 1.1 weight percent of the polyoxyethylene-based isocyanate-terminated prepolymer, 15 to 25 weight percent but preferably 18 weight percent alkylester of a carboxylic acid and 60 to 80 weight percent but preferably 79 weight percent toluene. The solution is mixed thoroughly until the polyvinylpyrrotidone and the prepolymer are completely dissolved. The component blending requires approximately one hour. The resulting lubricant coating solution should appear clear to pale yellow. The coating solution is naturally moisture sensitive and will increase in viscosity if not tightly capped during storage. Prior to coating medical devices with the present lubricant coating solution, the particular medical device, such as a catheter, should for best results be cleaned by first filling a container with 100% isopropanol. The medical device is then dip washed in the isopropanol for approximately 5 seconds and dried by forced air at approximately 50 to 90° C. to remove surface residual isopropanol and debris. The device should at this point be completely isopropanol free. The medical device is then dip coated for about 5 to 15 seconds in the lubricant coating vehicle solution slowly removed from the solution vat at a rate of about 0.5 inches per second. The catheter or other medical device is then air dried at room temperature for about 10 to 30 seconds to allow any excess lubricant coating solution to drain off. Optionally, excess lubricant may also be removed using absorbent towels. After air drying, the coated medical devices are optionally but preferably baked in forced air ovens at approximately 500 to 60°+/−5° for approximately 30 minutes to 3 hours but most preferably for one hour and then removed from the oven. Curing temperature and time are dependent upon the urethane pre-polymer and will vary according to concentrations. During curing, the diisocyanante reacts and becomes part of the polymer structure of the medical device. The medical devices are preferably checked for adequate transparency and to ensure that no solvent smell is present.

In packaging the subject medical devices coated in accordance with the present invention, the devices should not be allowed to touch one another. This is especially true if the environment humidity is high which could cause undesirable moisture absorption by the lubricant coating. To prevent or avoid such contact between the coated medical devices, each device may be packed in either paper, polyethylene tubing or the like depending on the shape of the particular device. If necessary, due to high atmospheric humidity, a desiccant may likewise be necessary in the packaging.

The preferred method of making and using the lubricant coating vehicle of the present invention is described in even greater detail in the following examples which are provided for purposes of further illustration. The following examples as described are not intended to be construed as limiting the scope of the present invention.

EXAMPLE 1

A lubricious coating was prepared by blending at room temperature the following components in a mixing vat for approximately 30 minutes until fully dissolved to form a crystal clear solution.

|  | wt % |
|---|---|
| Polyvinylpyrrolidone | 2.0 |
| Ethyl lactate | 18.0 |
| Toluene | 77.8 |
| Isocyanate-terminated prepolymer | 1.2 |

EXAMPLE 2

Thoracic catheters made of polyvinyl chloride (PVC) were washed with isopropanol and dried at 80° C. for 30 minutes. The catheters were dipped coated for 10 seconds while the catheters were still warm. After dipping, excessive coating was removed using paper towels. The catheters were then immediately baked at 80° C. for 60 minutes. The resultant coating was transparent and colorless with good bonding. The coating was very lubricious when wet. The friction reduction was up to 60%.

EXAMPLE 3

A lubricious coating vehicle was prepared by blending at room temperature the following components in a mixing vat for approximately 60 minutes until fully dissolved to form a crystal clear to pale yellow solution. The ingredients are mixed in order given due to miscibility of antibiotics in a particular solvent.

| Ingredient | % (wt) |
| --- | --- |
| THF | 30.0 g |
| Pellethane AE80 | 3.0 g |
| THF | 32.0 g |
| Tolnaftate | 1.0 g |
| NMP | 32.0 g |
| PVP K-90 | 1.0 g |
| Norfloxacin | 1.0 g |

The lubricious coating vehicle is prepared at room temperature. Mix until dissolved THF/Pellethane® AE80, add mixed THF/Tolnaftate solution to Pellethane® solution. NMP/PVP/Norfloxacin must be completely dissolved and then added to above solution. Allow to mix for 15 minutes at room temperature/tightly capped to prevent solvent evaporation. By adjusting the Pellethane® levels, not to exceed 5.0% and not going below 0.5%, one can adjust the release rate of antibiotics. These antibiotics are covalently bound to the urethane. Adjusting the PVP level does not increase/decrease release rate. The adjustment of the PVP level will make the device more/less lubricious.

EXAMPLE 4

A lubricious coating vehicle, containing silver salts for use on PVC medical devices, is prepared by blending at room temperature the following components in a mixing vat for approximately 60 minutes until fully dissolved to form a crystal clear to pale yellow solution. The order combination of the ingredients not imperative due to lack of covalent bonding of the silver salt to the urethane. The release of the silver salt is regulated by Pellethane® to PVP ratio adjustment due to entrapment/ionic bonding of the salt. The successful silver salts are: Giltech Powders 01-07 (this is a water soluble glass silver salt produced by Giltech Ltd.); AlphaSan RC2000 (this is a zirconium/phosphate crystal produced by Milliken Chemical); SSD (silver sulfadiazine) from Kendall's Oriskany Falls, N.Y. manufacturing facility; and silver oxide (obtained from Fisher Scientific). Heparin was added to the NMP/PVP solution in small quantities, 0.5–1.5%, qs. Cyclohexanone.

| Ingredient | % (wt) |
| --- | --- |
| THF | 30.0 g |
| Pellethane AE80 | 3.0 g |
| NMP | 32.0 g |

| Ingredient | % (wt) |
| --- | --- |
| PVP | 1.5 g |
| Silver Salt | 1.0%–3.0% |
| Cyclohexanone | 32.5 g |

The ingredients are mixed at room temperature in the above order. Once both parts have completely dissolved, the NMP(n-Methypyrrolidinone)/PVP/Cyclohexanone solution was added to the THF/Pellethane mixture. It was found that the PVP level should not exceed approximately 2.5% as it detrimentally affected coating adherence and silver release. Cyclohexanone was used to qs. solvent level. It is a less aggressive solvent for Pellethane and miscible with PVP and Heparin. Depending upon the silver complex used, the Cyclohexanone level was adjusted to maximize coating adherence to the PVC device. The amount of silver complex added to the formula is determined by the overall percent of silver loading within the salt complex. Giltech Powders range from 6%–9.5% silver loading (also, particle size of silver complex is very important in that it may cause problems in coating adherence. Larger particle size yielded poor coating adherence and uniformity,). SSD has 30% silver loading with sulfadiazine making up the bulk. AlphaSan has a range of 6.2%–10.0% silver loading.

Bio-compatibility Test

The coated catheters were first tested for hemolysis and then tested for lubricity using 1) protein adsorption and 2) platelet adhesion. The results of these tests show no hemolysis and improved lubricity as noted by a reduction of protein adsorption and platelet adhesion by more than 90% as set forth below.

1. Hemolysis

Using protein electrophoresis, no hemoglobin was seen in the supernatant of the PVP-coated thoracic catheter, nor was any seen in the hemolysis-negative control sample. As a comparison, rabbit hemoglobin was seen in gels stained with rabbit hemoglobin and the hemolysis-positive control. The results imply that the hydrophilic coating showed no sign of causing hemolysis.

2. Lubricity

Protein (Fibrinogen) Adsorption

Table 1 summarizes protein adsorption on the subject coated catheter surfaces and that of 15 the control samples.

TABLE 1

| Material | n | ng | ng/cm$^2$" |
| --- | --- | --- | --- |
| Control | 4 | 1620 ± 69 | 339.3 ± 14.4 |
| PVP-coated | 4 | 87.6 ± 27.1 | 18.3 ± 5.7 |

": ID = 0.4 cm, total surface area of 3.8 cm tubing = 4.7 cm$^2$

Test results show the adsorption of fibrinogen onto the hydrophilic surface was decreased by more than 90% compared to control surface.

Platelet Adhesion

Table 2 summarizes platelet adhesion on the subject coated catheter surfaces and that of the control samples:

TABLE 2

| Material | n | Platelet/cm$^2$ (×10$^5$) |
| --- | --- | --- |
| Control | 4 | 7.246 ± 0.052 |
| PVP-coated | 4 | 0.055 ± 0.019 |

Table 2 illustrates the platelet adhesion on both the PVP coated and control catheters. The hydrophilic coating reduced platelet adhesion by more than 95%. The difference in platelet adhesion was further characterized by Scanning Electron Microscope (SEM) which showed control catheters having numerous platelets attached to the surface thereof while the subject PVP-coated catheters showed little sign of platelet adhesion.

The subject lubricant composition prepared in accordance with the present invention may be applied as a thin surface film, e.g., less than about 4.0 mil but most preferably less than about 2.5 mil-in thickness, which upon contact with water or fluid sufficiently reduces the coefficient of friction to aid in the in vivo placement of medical devices.

The unexpected significant advantages of the present lubricious coating vehicle achieved through the particular composition formulation noted above include decreased wet coefficient of friction, decreased adherence with various surfaces, resistance to wet abrasion and efficacious anti-microbial properties.

Medical devices once coated with the lubricious coating vehicle of the present invention are to be packaged and sterilized using an appropriate sterilization technique or may be sterilized and then packaged using aseptic technique. Appropriate methods of sterilization and packaging are known to those skilled in the art and include gamma radiation, electronic beam, ethylene oxide, and like methods. Preferably, medical devices coated with the subject lubricious coating are packaged and then sterilized using gamma radiation by cobalt 60 with 1 to 3 mrads but preferably 2 mrads in two independent exposure cycles for superior results.

Appropriate packaging for the subject coated medical devices includes metallic foil pouches such as aluminum foil pouches, polyethylene film, ethylene vinyl acetate film, polypropyrene film, polyvinyl chloride film and like packages known to those skilled in the art, but preferably, an aluminum foil cover pouch with an ethylene vinyl acetate film, inner liner to prevent moisture absorption by the lubricant.

The method of using the subject coated medical devices comprises removing the device from its packaging, applying moisture to the lubricated surface of the device and placing the device as necessary for a particular medical procedure.

It is seen therefore that the present lubricious coating vehicle for medical devices provides an effective wet abrasion resistant, low coefficient of friction coating for medical devices and a vehicle for delivering additives such as anti-microbials and other pharmacological active compounds. Additionally, the ability of the urethane within the lubricious coating vehicle to covalently bond anti-thrombogenic agents such as heparin is utilized to prevent systemic absorption. The lubricious coating vehicle, the method of making and using the lubricious coating vehicle, the coated medical devices and the method of using the coated medical devices as disclosed and described herein have specific advantages over the heretofore known lubricants for medical devices. The subject lubricious coating vehicle resists wet abrasion, adheres to a variety of surfaces, has a decreased coefficient of friction only when wetted, is biocompatible, and is able to deliver pharmacological active agents with acceptable pharmacokinetic properties. Hence for these reasons, as well as others, some of which herein above set forth, it is seen that the present lubricious coating vehicle represents a significant advancement in the art which has substantial commercial significance.

Although the lubricious coating vehicle described in the illustrative embodiments herein are a series of coatings pertaining to anti-microbial additives and the methods for ensuring that the pharmcokinectics are within efficacious ranges; it should be appreciated that additives within the lubricious coating vehicle could be other desirable pharmaceutical active compounds such as topical anesthetics, anti-inflammatory compounds both non-steroidal and steroidal, spermicidal compounds, or the like. Similarly, rather than the traditional pharmaceutical compounds the additives can be organic compounds with desired pharmacological effects.

The foregoing has been a description of an illustrative embodiment of the present invention. The present invention is not to be limited in scope by the illustrative embodiments described which are intended as specific illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims

What is claimed is:

1. A medical article lubricant composition that allows the release of a pharmacological additive said lubricant composition comprising: an alkylbenzene, a polymer selected from the group consisting of polyvinyl alcohol, polyacrylic acid and polyethylene oxide, an isocyanate-terminated prepolymer, an alkylester of a carboxylic acid, and a pharmacological additive having anti-microbial properties.

2. The composition of claim 1 wherein said alkylbenzene is selected from the group consisting of toluene, xylene and styrene.

3. The composition of claim 1 wherein said alkylbenzene is toluene.

4. The composition of claim 1 wherein said alkylbenzene is selected from the group consisting of C1–12 alkylbenzenes.

5. The composition of claim 1 wherein said alkylester of a carboxylic acid is selected from the group consisting of ethyl lactate, methylbenzoate and propolyacrylate.

6. The composition of claim 1 wherein said alkylester of a carboxylic acid is ethyl lactate.

7. The composition of claim 1 wherein said alkylester of a carboxylic acid is selected from the group consisting of C1–12 alkylesters of carboxylic acids.

8. The composition of claim 1 wherein said isocyanate-terminated prepolymer is selected from the group consisting of polyoxyethylene-based isocyanate prepolymers.

9. The composition of claim 1 wherein said isocyanate-terminated prepolymer is selected from the group consisting of toluene aid isophorone diisocyanate-based prepolymers.

10. The composition of claim 1 wherein said pharmacological additive is an anti-microbial selected from a group consisting of chorhexidine acetate, chlorhexidine gluconate, chlorhexidine hydrochloride, chlorhexidine sulfate, silver acetate, silver benzoate, silver carbonate, silver iodate, silver iodide, silver lactate, silver chloride, silver laurate, silver nitrate, silver oxide, silver palmitate, silver protein, silver sulfadiazine, polymyxin, tetracycline, tobramycin, gentamicin, rifampician, bacitracin, neomycin, chloramphenical, oxolinic acid, norfloxacin, nalidix acid, pefloxacin, enoxacin and ciprofloxacin, penicillin, ampicillin, amoxicillin, piracil, cephalosporins and vancomycin.

11. A method for producing a lubricant composition for a medical article, said lubricant composition allowing for the release of a pharmacological additive, said method comprising: blending an alkylbenzene, a polymer selected from the group consisting of polyvinyl alcohol, polyacrylic acid and polyethylene oxide, an isocyanate-terminated prepolymer, an alkylester of a carboxylic acid, and a pharmacological additive having anti-microbial properties until dissolved.

12. The method of claim 11 wherein said alkylbenzene is selected from the group consisting of toluene, xylene and styrene.

13. The method of claim 11 wherein said alkylbenzene is toluene.

14. The method of claim 11 wherein said alkylbenzene is selected from the group consisting of C1–12 alkylbenzenes.

15. The method of claim 11 wherein said alkylester of a carboxylic acid is selected from the group consisting of ethyl lactate, methylbenzoate and propolyacrylate.

16. The method of claim 11 wherein said alkylester of a carboxylic acid is ethyl lactate.

17. The method of claim 11 wherein said alkylester of a carboxylic acid is selected from the group consisting of C1–12 alkylesters of carboxylic acids.

18. The method of claim 11 wherein said isocyanate-terminated prepolymer is selected from the group consisting of polyoxyethylene-based isocyanate prepolymers.

19. The method of claim 11 wherein said isocyanate-terminated prepolymer is selected from the group consisting of toluene diisocyanate-based prepolymers.

20. The method of claim 11 wherein said pharmcological additive is selected from a group consisting of chorhexidine acetate, chlorhexidine gluconate, chlorhexidine hydrochloride, chlorhexidine sulfate, silver acetate, silver benzoate, silver carbonate, silver iodate, silver iodide, silver lactate, silver chloride, silver laurate, silver nitrate, silver oxide, silver palmitate, silver protein, silver sulfadiazine, polymyxin, tetracycline, tobramycin, gentamicin, rifampician, bacitracin, neomycin, chloramphenical, oxolinic acid, norfloxacin, nalidix acid, pefloxacin, enoxacin and ciprofloxacin, penicillin, ampicillin, amoxicillin, piracil, cephalosporins and vancomycin.

* * * * *